(12) United States Patent
Boudreau et al.

(10) Patent No.: US 9,778,230 B2
(45) Date of Patent: Oct. 3, 2017

(54) ULTRASOUND SCANNING SYSTEM, ASSEMBLY, AND METHOD FOR INSPECTING COMPOSITE STRUCTURES

(71) Applicant: THE BOEING COMPANY, Chicago, IL (US)

(72) Inventors: Kate Boudreau, Seattle, WA (US); Justin D. Serrill, Issaquah, WA (US); Fred D. Young, Bellevue, WA (US)

(73) Assignee: The Boeing Company, Chicago, IL (US)

(*) Notice: Subject to any disclaimer, the term of this patent is extended or adjusted under 35 U.S.C. 154(b) by 291 days.

(21) Appl. No.: 14/700,954

(22) Filed: Apr. 30, 2015

(65) Prior Publication Data

US 2016/0320348 A1    Nov. 3, 2016

(51) Int. Cl.
| | |
|---|---|
| *B64F 5/60* | (2017.01) |
| *G01N 29/04* | (2006.01) |
| *G01N 29/24* | (2006.01) |
| *G01N 29/26* | (2006.01) |
| *G01N 29/44* | (2006.01) |

(Continued)

(52) U.S. Cl.
CPC ............ *G01N 29/265* (2013.01); *B64F 5/60* (2017.01); *G01N 29/04* (2013.01); *G01N 29/11* (2013.01); *G01N 29/225* (2013.01); *G01N 29/24* (2013.01); *G01N 29/2456* (2013.01); *G01N 29/2493* (2013.01); *G01N 29/262* (2013.01); *G01N 29/4436* (2013.01); *G01N 2291/0231* (2013.01); *G01N 2291/106* (2013.01); *G01N 2291/263* (2013.01)

(58) Field of Classification Search
CPC ...... G01N 29/265; G01N 29/24; G01N 29/04; G01N 2291/0231; G01N 2291/106; G01N 2291/263
USPC .......................................................... 73/625
See application file for complete search history.

(56) References Cited

U.S. PATENT DOCUMENTS

| | | | | |
|---|---|---|---|---|
| 5,810,809 A | * | 9/1998 | Rydell ............ | A61B 17/32002 604/22 |
| 6,722,202 B1 | | 4/2004 | Kennedy | |

(Continued)

FOREIGN PATENT DOCUMENTS

| | | | |
|---|---|---|---|
| CN | 105147335 | * | 12/2015 |
| DE | 2337357 | * | 11/1975 |

(Continued)

OTHER PUBLICATIONS

Extended European Search Report for EP 16163275.7-1554, dated Sep. 5, 2016.

*Primary Examiner* — J M Saint Surin
(74) *Attorney, Agent, or Firm* — Joseph M. Butscher; The Small Patent Law Group, LLC (57) ABSTRACT

An ultrasound scanning assembly is configured to inspect a structure, such as a composite winglet of an aircraft. The ultrasound scanning assembly may include an outer ultrasound probe configured to be positioned on an outer surface of the structure. The outer ultrasound probe may include a phased array transducer having a plurality of transducer elements. An inner ultrasound probe may be configured to be positioned within the structure opposite from the outer surface. The inner ultrasound probe may include a single element transducer configured to receive ultrasound signals transmitted by the phased array transducer.

20 Claims, 7 Drawing Sheets

(51) Int. Cl.
*G01N 29/265* (2006.01)
*G01N 29/11* (2006.01)
*G01N 29/22* (2006.01)

(56) References Cited

U.S. PATENT DOCUMENTS

| | | |
|---|---|---|
| 7,050,535 B2 | 5/2006 | Georgeson |
| 7,320,249 B2 | 1/2008 | Georgeson |
| 7,444,876 B2 | 11/2008 | Sarr |
| 7,617,732 B2 | 11/2009 | Bui |
| 7,640,811 B2 | 1/2010 | Kennedy |
| 7,762,120 B2 | 7/2010 | Vaccaro |
| 9,250,123 B2 * | 2/2016 | Hardegger ............... H01L 33/60 |
| 9,414,026 B2 * | 8/2016 | Blanchard ................ H04N 7/18 |
| 2006/0162456 A1 * | 7/2006 | Kennedy .............. G01N 29/225 |
| | | 73/620 |
| 2006/0201252 A1 | 9/2006 | Georgeson |
| 2010/0095775 A1 | 4/2010 | Sarr |
| 2011/0146424 A1 * | 6/2011 | Sarr ....................... G01N 27/82 |
| | | 73/866.5 |

FOREIGN PATENT DOCUMENTS

| | | |
|---|---|---|
| EP | 1744156 | 1/2007 |
| EP | 2045600 | 4/2009 |
| JP | 2004279181 | * 10/2004 |
| JP | 2009236561 | * 10/2009 |

\* cited by examiner

ULTRASOUND SCANNING SYSTEM, ASSEMBLY, AND METHOD FOR INSPECTING COMPOSITE STRUCTURES

FIELD OF THE DISCLOSURE

Embodiments of the present disclosure generally relate to ultrasound scanning systems, assemblies, and methods for inspecting composite structures, which may be used to form portions of an aircraft.

BACKGROUND OF THE DISCLOSURE

Various structural components are used to form a typical aircraft. For example, wing and empennage surfaces of an aircraft typically include stringers that are coupled to skin members on the wing and empennage surfaces that cooperatively provide a desired flexural and torsional stiffness to the wing and empennage surfaces.

Aircraft structures may be formed from composite materials, which are generally reinforced polymer-based materials used in place of metals, particularly in applications in which relatively low weight and high mechanical strength is desired. Composite materials are widely used in a variety of commercial and military aircraft, terrestrial vehicles and consumer products. A composite material may include a network of reinforcing fibers that are generally applied in layers, and a polymeric resin that substantially wets the reinforcing fibers to form a binding contact between the resin and the reinforcing fibers. The composite material may then be formed into a structural component by a variety of known forming methods, such as an extrusion process or other forming processes.

Certain aircraft include winglets extending from distal ends of main wing structures. Winglets are configured to reduce drag, such as by partially recovering tip vortex energy. Various winglets are configured to increase lift generated at the wingtip (by smoothing airflow across the upper wing near the tip) and reduce lift-induced drag caused by wingtip vortices, thereby improving lift-to-drag ratio.

Ultrasound probes may be used to scan structures (such as composite or metal wings, fuselage, and the like of an aircraft) to assess a condition of the structure. Nondestructive inspection (NDI) techniques are used to inspect leading edges of winglets. For example, NDI techniques are used to detect imperfections, such as delaminations, in composite winglets. The leading edge of a winglet generally includes an asymmetrically shaped parabolic cross section that varies in size and shape between inboard and outboard areas.

Ultrasonic inspection of composite structures generally includes pulsing and receiving elements that are disposed normal to a surface of the part being inspected. Due to the asymmetric size and shape of winglets, however, such normal orientation may be difficult or impossible to achieve.

Accordingly, a need exists for a system and method for efficiently inspecting an irregularly-shaped composite structure, such as a winglet of an aircraft.

SUMMARY OF THE DISCLOSURE

Certain embodiments of the present disclosure provide an ultrasound scanning assembly configured to inspect a structure, such as a composite winglet. The ultrasound scanning assembly may include an outer ultrasound probe configured to be positioned on an outer surface of the structure. The outer ultrasound probe may include a phased array transducer having a plurality of transducer elements. An inner ultrasound probe may be configured to be positioned within the structure opposite from the outer surface. The inner ultrasound probe may include a single element transducer configured to receive ultrasound signals transmitted by the phased array transducer. One or both of the outer and inner ultrasound probes may include at least one magnet that magnetically couples the outer and inner ultrasound probes together.

The phased array transducer may include a radially curved transmission surface. The single element transducer may include a convex lens.

In at least one embodiment, the outer ultrasound probe may include a main housing that retains the phased array transducer, and one or more wheels rotatably secured to the main housing. The wheel(s) may be configured to directly contact the outer surface of the structure. The outer ultrasound probe may also include one or more magnets coupled to the main housing. The magnet(s) may be configured to magnetically couple the outer ultrasound probe to the inner ultrasound probe. In at least one embodiment, the phased array transducer may be configured to be selectively secured at different positions of the main housing. The main housing may include an inner curved surface that is configured to conform to the outer surface of the structure.

In at least one embodiment, the inner ultrasound probe may include a main housing that retains the single transducer element, and one or more wheels rotatably secured to the main housing. The wheel(s) may be configured to directly contact an inner surface of the structure.

The outer ultrasound probe may include at least one inwardly-biased pivot arm that is configured to conform to the outer surface of the structure. The inner ultrasound probe may include at least one outwardly-biased pivot arm that is configured to conform to an inner surface of the structure.

Certain embodiments of the present disclosure provide an ultrasound scanning system configured to inspect a composite winglet. The ultrasound scanning system may include an ultrasound scanning assembly including an outer ultrasound probe configured to be positioned on an outer surface of the composite winglet. The outer ultrasound probe may include a phased array transducer having a plurality of transducer elements. The ultrasound scanning assembly may also include an inner ultrasound probe magnetically coupled to the outer ultrasound probe. The inner ultrasound probe may be configured to be positioned within an internal cavity of the composite winglet and abut into an inner surface of the composite winglet that is opposite from the outer surface. The inner ultrasound probe may include a single element transducer configured to receive ultrasound signals transmitted by the phased array transducer. The ultrasound scanning system may also include a control unit in communication with the ultrasound scanning assembly. The control unit may be configured to compare a transmit signal strength of ultrasound signals transmitted from the outer ultrasound probe with a receive signal strength of the ultrasound signals received by the single element transducer. The control unit is configured to determine an existence of one or more imperfections within the composite winglet by comparing the transmit signal strength with the receive signal strength.

Certain embodiments of the present disclosure provide a method for inspecting a composite winglet. The method may include positioning an outer ultrasound probe on an outer surface of the composite winglet, positioning an inner ultrasound probe within the composite winglet, magnetically coupling the outer ultrasound probe to the inner ultrasound probe, transmitting ultrasound signals from a radially-curved transmission surface of a phased array transducer of the outer ultrasound probe through the composite winglet toward a single element transducer of the inner ultrasound probe, comparing a transmit signal strength of the ultrasound signals transmitted from the phased array transducer to a receive signal strength of the ultrasound signals received by the single element transducer, confirming a structural integrity of the composite winglet in response to the receive signal strength agreeing with the transmit signal strength, and indicating a presence of an imperfection within the composite winglet in response to the receive signal strength differing from the transmit signal strength. The method may also include moving the outer ultrasound probe over the outer surface of the composite winglet, and moving the inner ultrasound probe through the interior of the composite winglet in response to the outer ultrasound probe moving over the outer surface of the composite winglet (such as through the magnetic coupling).

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide systems and methods for non-destructively inspecting (such as through use of ultrasound signals) a structure, which may include one or more irregularly-shaped surfaces. For example, embodiments of the present disclosure may be used to ultrasonically inspect a leading edge region of a composite winglet.

The systems and methods may include an outer ultrasound probe having a curved ultrasound phased array that is used to pulse one or more ultrasonic signals outside of the structure toward an inner ultrasound probe having a single element transducer temporarily positioned within a portion of the structure. The outer and inner ultrasound probes may be magnetically coupled together, such that at least a portion of the structure being inspected is positioned between the outer and inner ultrasound probes. The systems and methods may employ through transmission ultrasound, instead of pulse echo ultrasound. Accordingly, the outer ultrasound probe transmits one or more ultrasound signals that are received by the inner ultrasound probe. A control unit may monitor the signals received by the inner ultrasound probe to determine signal strength. Signal loss may be indicative of an imperfection with the structure, such as an inter-ply delamination of a composite structure. Embodiments of the present disclosure provide systems and methods of inspecting a complex, asymmetrically-curved composite structure, for example.

Certain embodiments of the present disclosure provide systems and methods that may include an outer ultrasound probe having a radially curved phased array, and an inner ultrasound probe having a convex single element transducer that is configured to receive transmitted signals from the phased array of the outer ultrasound probe. In contrast to pulse echo systems, embodiments of the present disclosure are configured to adapt to and accurately inspect structures having irregularly shaped surfaces.

Certain embodiments of the present disclosure provide systems and methods that are configured to use separate and distinct ultrasound probes on opposite sides of a surface of a composite structure, such as a winglet. An outer ultrasound probe may include a phased array that is used as an ultrasonic signal transmitter. An inner ultrasound probe may include a single element transducer that is used as an ultrasonic signal receiver. The single element transducer may include a lens having a convex curvature that is configured to receive transmitted ultrasound signals from a wide coverage angle. The outer and inner ultrasound probes may be magnetically coupled together. In this manner, the inner ultrasound probe may move in response to the outer ultrasound probe, even though the inner ultrasound probe may be disposed within a confined space of a composite structure.

Certain embodiments of the present disclosure provide a method for through transmission ultrasound scanning of a composite structure for nondestructive inspection. The method may include enabling an ultrasound scanner, spatially positioning ultrasound transducer elements that may provide a stereo pulse emission at an angle relative to each other, and enabling detection of a through transmission pulse using a single sensor element. The angled stereo pulse emission configuration enables a scan through the composite structure for detecting composite structure inter-ply delamination. The transducer elements and the sensor element may be magnetically coupled together, thereby providing a substantially fixed corresponding spatial coordination between the transducer and sensor elements. The composite structure may be a curved structure including a leading edge region, such as an upper or lower composite winglet of an aircraft. The transducer elements may include or otherwise provide a radially curved phased array pulse generator. The sensor element may include a convex single element ultrasonic transducer lens.

Figure 1:
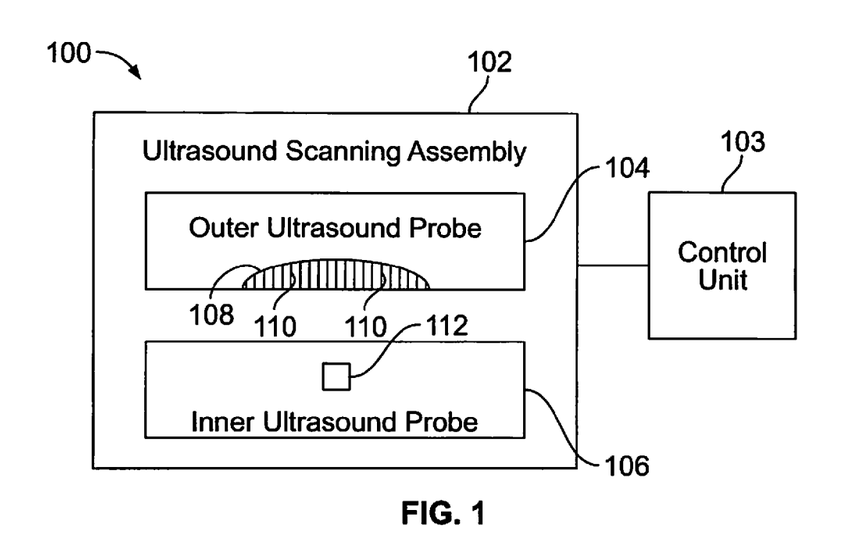
FIG. 1 illustrates a schematic block diagram of an ultrasound scanning system that is configured to non-destructively inspect a structure, according to an embodiment of the present disclosure.

FIG. 1 illustrates a schematic block diagram of an ultrasound scanning system 100 that is configured to non-destructively inspect a structure, according to an embodiment of the present disclosure. For example, the ultrasound scanning system 100 may be used to non-destructively inspect a structure having one or more irregularly-shaped or curved surfaces, such as a winglet that is to connect to or otherwise form part of a wing structure of an aircraft.

The ultrasound scanning system 100 may include an ultrasound scanning assembly 102 and a control unit 103 that may be in communication with the ultrasound scanning assembly 102. For example, the control unit 103 may be operatively coupled to the ultrasound scanning assembly through a wired or wireless connection. The control unit 103 may be configured to receive output inspection signals from the ultrasound scanning assembly 102. For example, the output inspection signals may be or include signals that are output from the inner ultrasound probe 106 and/or the outer ultrasound probe 104. The control unit 103 analyzes the inspection signals to detect a receive signal strength, which may, in turn, relate to an integrity of a structure that is being inspected.

The ultrasound scanning assembly 102 may include an outer ultrasound probe 104 and an inner ultrasound probe 106. The outer and inner ultrasound probes 104 and 106 are separate and distinct from one another. The outer ultrasound probe 104 is configured to be positioned on an outer surface of a structure, while the inner ultrasound probe 106 is configured to be positioned on an inner surface of a structure. For example, the outer ultrasound probe 104 may be disposed on an outer surface of a composite winglet, while the inner ultrasound probe 106 may be positioned within the composite winglet and may abut into an inner surface of the composite winglet. The outer ultrasound probe 104 may be magnetically coupled to the inner ultrasound probe 106. The magnetic coupling between the outer and inner ultrasound probes 104 and 106 allows for a portion of the structure to be positioned therebetween. As the outer ultrasound probe 104 translates or otherwise moves over an outer surface of the structure, the inner ultrasound probe 106 moves in response thereto within the structure due to the magnetic coupling between the outer and inner ultrasound probes 104 and 106.

The outer ultrasound probe 104 may include a pulse generator, such as a phased array transducer 108 having a plurality of ultrasound elements 110. The inner ultrasound probe 106 may include a sensor, such as a single element ultrasound transducer 112. Due to the small size of the single element ultrasound transducer 112 reduces the overall size of the inner ultrasound probe 106, which allows the inner ultrasound probe 106 to be inserted into tight, confined spaces, such as within a winglet. Alternatively, the inner ultrasound probe 106 may include a sensor other than a single element transducer 112. For example, the sensor may be or include multiple transducer elements.

In at least one embodiment, the control unit 103 may compare the receive signal strength of one or more signals output by the inner ultrasound probe 106 with a transmit signal strength of one or more signals output by the outer ultrasound probe 104. The control unit 103 compares the receive and transmit signal strengths in order to determine the existence of imperfections within the structure. If, for example, the receive and transmit signal strengths agree with one another (that is, are generally the same, but may include expected differences, which may occur through signal attenuation through the structure), then the control unit 103 may determine that the structure is structurally sound (for example, no imperfections). If, however, the receive and transmit signal strengths differ with each other to an extent greater than expected, then the control unit 103 may determine that the structure includes at least one imperfection (such as an inter-ply delamination within a composite structure).

In operation, the outer ultrasound probe 104 and the inner ultrasound probe 106 are positioned on opposite sides or surfaces of a structure to be inspected. As noted, the outer and inner ultrasound probes 104 and 106 may be magnetically coupled to one another, thereby remaining in a substantially secure relationship to one another despite the structure being positioned therebetween. In order to inspect the structure, the control unit 103 may operate the outer ultrasound probe 104 to transmit a plurality of ultrasound signals from the phased array transducer 108 toward the single element ultrasound transducer 112 through the structure. The single element ultrasound transducer 112 receives the transmitted ultrasound signals from the phased array transducer 108.

The control unit 103 may be in communication with one or both of the outer ultrasound probe 104 and/or the inner ultrasound probe 106. As such, the control unit 103 may compare the signal strength of the transmitted ultrasound signals (that is, the transmit signal strength) from the outer ultrasound probe 106 with the signal of the ultrasound signals as they are received by the inner ultrasound probe 106 (that is, the receive signal strength). If the transmitted and received signal strengths are the same (or substantially the same), then the control unit 103 may confirm the integrity of the structure that is being inspected. For example, the control unit 103 may cause an audible signal to be broadcast (such as through a speaker connected to a computer) or visual confirmation signal to be displayed, such as on a display connected to a computer. If, however, the receive signal strength is less than the transmit signal strength, the control unit 103 may determine that an imperfection, such as inter-ply delamination, is present within the structure.

It is to be understood that an expected amount of signal attenuation may occur as the ultrasound signals are transmitted through the structure. For example, as an ultrasound signal travels through layers of composite material, a portion of the signal strength may be absorbed or otherwise attenuated by one or more of the layers. The control unit 103 may account for such expected attenuation. Thus, the control unit 103 may compare a receive signal strength with a transmit signal strength to determine if they agree with one another. For example, the signals agree when the receive signal strength is a value (or within an expected range of values) in relation to the transmit signal strength that is related to a structurally sound structure, such as a structurally sound winglet. In contrast, if the receive signal strength is not at the value (or within the expected range of values), the receive signal strength differs from the transmit signal strength (for example, being less than an expected value or within an expected range of values), and, as such, the structure is not structurally sound.

As used herein, the term "controller," "control unit," "unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor capable of executing the functions described herein. Such are exemplary only, and are thus not intended to limit in any way the definition and/or meaning of such terms.

The control unit 103 may be configured to execute a set of instructions that are stored in one or more storage elements (such as one or more memories), in order to process data. For example, the control unit 103 may include one or more memories. The storage elements may also store data or other information as desired or needed. The storage element may be in the form of an information source or a physical memory element within a processing machine.

The set of instructions may include various commands that instruct the control unit 103 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units. It is to be understood that the processing or control units may represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control units may represent processing circuitry such as one or more of a field programmable gate array (FPGA), application specific integrated circuit (ASIC), microprocessor(s), a quantum computing device, and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
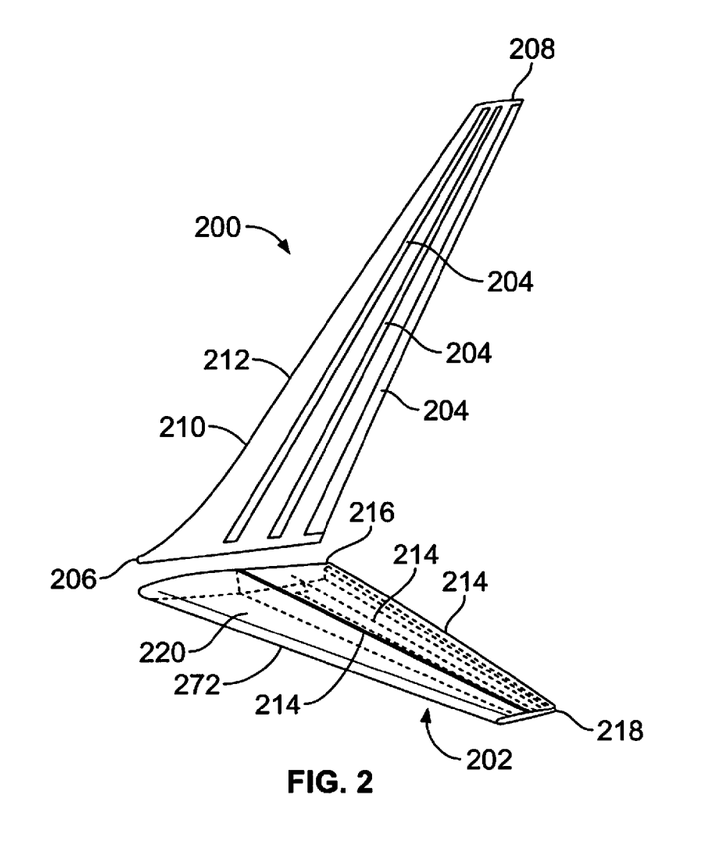
FIG. 2 illustrates a perspective lateral view of an upper winglet and a lower winglet, according to an embodiment of the present disclosure.
Figure 3:
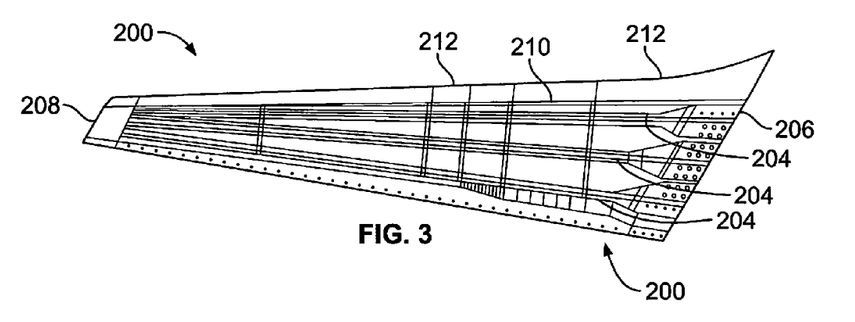
FIG. 3 illustrates a lateral view of an upper winglet, according to an embodiment of the present disclosure.
Figure 4:
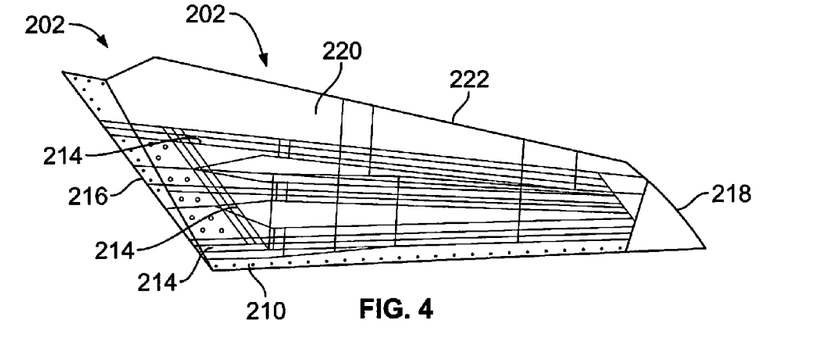
FIG. 4 illustrates a lateral view of a lower winglet, according to an embodiment of the present disclosure.

FIG. 2 illustrates a perspective lateral view of an upper winglet 200 and a lower winglet 202, according to an embodiment of the present disclosure. FIG. 3 illustrates a lateral view of the upper winglet 200. FIG. 4 illustrates a lateral view of the lower winglet 202. Referring to FIG. 104, the upper and lower winglets 200 and 202 are examples of structures that may be inspected by the ultrasound scanning system 100.

The upper winglet 200 may include support spars 204 that extend from an inboard end 206 to an outboard tip 208. The term inboard means closer to a central longitudinal plane of a fuselage of an aircraft, while the term outboard means further from the central longitudinal plane of the fuselage of the aircraft. As shown, the upper winglet 200 may include three support spars 204 that extend along a length of the upper winglet 200. Alternatively, the upper winglet 200 may include more or less support spars 204 than shown. The support spars 204 are used to support an outer composite skin 210, which may be formed of multiple plies of composite material laminated together. The upper winglet 200 also includes a curved leading edge 212 that extends from the inboard end 206 to the outboard tip 208.

Similar to the upper winglet 200, the lower winglet 202 may include support spars 214 that extend from an inboard end 216 to an outboard tip 218. As shown, the lower winglet 202 may include three support spars 214 that extend along a length of the lower winglet 202. Alternatively, the lower winglet 202 may include more or less support spars 214 than shown. The support spars 214 are used to support an outer composite skin 220, which may be formed of multiple plies of composite material laminated together. The lower winglet 202 also includes a curved leading edge 222 that extends from the inboard end 216 to the outboard tip 218.

Figure 5:
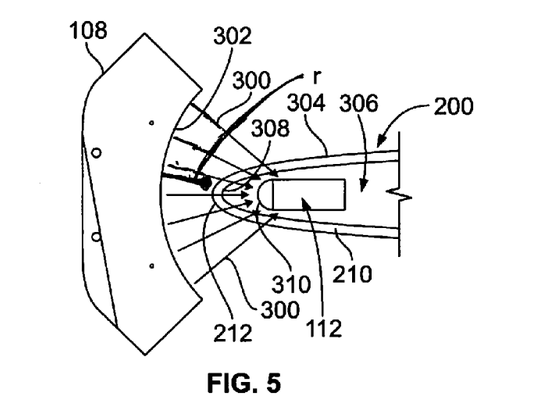
FIG. 5 illustrates a simplified end view of a phased array transducer transmitting ultrasound signals through a curved leading edge of an upper winglet toward a single element transducer, according to an embodiment of the present disclosure.

FIG. 5 illustrates a simplified end view of the phased array transducer 108 transmitting ultrasound signals 300 through the curved leading edge 212 of the upper winglet 200 toward the single element transducer 112, according to an embodiment of the present disclosure. Referring to FIGS. 1 and 5, the phased array transducer 108 is part of the outer ultrasound probe 104, while the single element transducer 112 is part of the inner ultrasound probe 106. While the upper winglet 200 is shown in FIG. 5, it is to be understood that the phased array transducer 108 and the single element transducer 112 may be used in relation to the lower winglet 202 (shown in FIGS. 2 and 4). Indeed, embodiments of the present disclosure may be used with respect to any structure that is to be ultrasonically inspected.

The phased array transducer 108 may include an inwardly-curved or concave transmission surface 302. For example, the transmission surface 302 may include a curvature defined by a constant radius r. Optionally, the radius of the curvature may vary at different points along the transmission surface 302. The transmission surface 302 may be curved in order to direct each of the ultrasound signals 300 toward the single element transducer 112. For example, the phased array transducer 108 may include a plurality of transducer elements, each of which is configured to transmit a separate ultrasound signal 300 toward the single element transducer 112. In at least one embodiment, the phased array transducer 108 may include forty individual single element transducers. Optionally, the phased array transducer 108 may include more or less than forty individual single element transducers.

As shown, the phased array transducer 108 is disposed outside of the upper winglet 200. For example, the outer ultrasound probe 104 may abut into an outer surface 304 of the upper winglet 200. As noted, the outer ultrasound probe 104 is magnetically coupled to the inner ultrasound probe 106. In this manner, the inner ultrasound probe 106, which is disposed within an internal cavity 306 of the upper winglet 200, is magnetically attracted to the outer ultrasound probe 104 and is biased toward the outer ultrasound probe 104 into an inner surface 308 of the upper winglet 200. As the outer ultrasound probe 104 translates or otherwise moves over the outer surface 304, the inner ultrasound probe 106 translates or otherwise moves within the internal cavity 306 in response to the movement of the outer ultrasound probe 104.

The single element transducer 112 may include an outer convex lens 310. The outer convex lens 310 may have an outwardly-biased curve that may be reciprocal to the shape of the transmission surface 302. Optionally, the outer convex lens may have an outwardly-biased curve that is not reciprocal to the shape of the transmission surface 302. The outer convex lens 310 is configured to receive the ultrasound signals 300 over a wide coverage area. For example, the outer convex lens 310 may be configured to receive ultrasound signals within a semispherical coverage volume emanating from the outer convex lens 310.

The system 100 may employ through transmission ultrasound. As shown in FIG. 5, the phased array transducer 108 transmits the ultrasound signals 300 through the curved leading edge 212. The single element transducer 112 within the internal cavity 306 receives the ultrasound signals 300. If the composite skin 210 includes imperfections, such as delaminations between plies of composite material, the transmitted ultrasound signals 300 may bounce or otherwise be redirected away from the single element transducer 112. The control unit 103 monitors the signal strength of the ultrasound signals 300 as they are transmitted from the phased array transducer 108, and as the ultrasound signals 300 are received by the single element transducer 112. If a difference exists between the transmitted signal strength at the point of transmission at or proximate to the transmission surface 302 and the received signal strength at the single element transducer 112, the control unit 103 may determine that an imperfection, such as an inter-ply delamination, is present within the curved leading edge 212.

Figure 6:
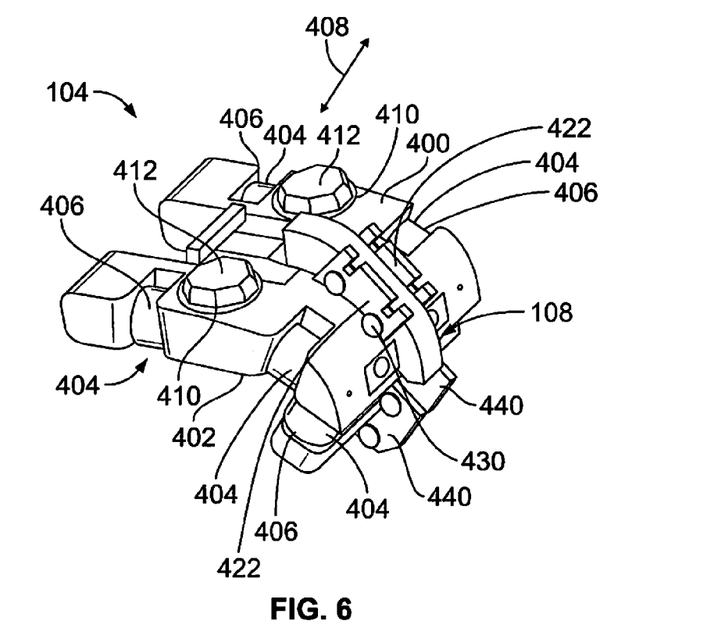
FIG. 6 illustrates a perspective top view of an outer ultrasound probe, according to an embodiment of the present disclosure.

FIG. 6 illustrates a perspective top view of the outer ultrasound probe 104, according to an embodiment of the present disclosure. As an example, the outer ultrasound probe 104 may be a 2.25 MHz, forty element, 1.625" radius pulsing ultrasound probe. Alternatively, the outer ultrasound probe 104 may be various other types. The outer ultrasound probe 104 may include a main housing 400, which may include an interior curved surface 402, which may conform to an outer curved surface of a leading curved edge of a winglet, such as those described above. Alternatively, the main housing 400 may be sized and shaped differently than shown. The main housing 400 may be formed of various materials, such as plastics, Nylon, stainless steel, and/or the like.

One or more roller chambers 404 may be formed within portions of the main housing 400. Each of the roller chambers 404 is configured to rotatably retain a wheel 406, which may include an inner hub and outer contacting surface, each of which may be formed of rubber, for example. The wheels 406 allow the main housing 400 to easily and smoothly roll over a surface of the structure in the directions of arrows 408. Alternatively, the outer ultrasound probe 104 may not include the wheels 406.

The main housing 400 may also include one or more magnet chambers 410 covered by caps 412. Each of the caps 412 may be removed, such as through a threadable engagement, to expose magnets within the magnet chambers 410. The magnets within the magnet chambers 410 are configured to magnetically couple to one or more attractive elements, such as a metal component, additional magnets, and/or the like, contained or positioned on the inner ultrasound probe 106 (shown in FIG. 1, for example).

The main housing 400 may also include opposed transducer securing brackets 422 separated by a space. The phased array transducer 108 is positioned between the opposed transducer securing brackets 422. One or more fasteners 430, such as bolts, rods, posts, screws, or the like, securely connect to the securing brackets 422 and securely retain the phased array transducer 108 between the securing brackets 422.

An additional set of opposed securing brackets 440 may extend from the main housing 400 below the securing brackets 422. In this manner, the phased array transducer 108 may be selectively moved between different positions of the main housing 400. The phased array transducer 108 may be selectively moved between the securing brackets 422 and the securing brackets 440. In this manner, the phased array transducer 108 may be configured to transmit ultrasound signals from different positions, such as from an upper portion and a lower portion of the outer ultrasound probe 104. Alternatively, the outer ultrasound probe 104 may include only one set of securing brackets. As another alternative, the outer ultrasound probe 104 may include more than two sets of securing brackets to provide additional positions for the phased array transducer 108. Further, other securing structures and fasteners may be used to secure the phased array transducer 108 in position. For example, in at least one embodiment, the phased array transducer 108 may be adhesively secured in position. In at least one other embodiment, the phased array transducer 108 may be configured to removably secure to the main housing through one or more of snaps, latches, an interference fit, and/or the like.

Figure 7:
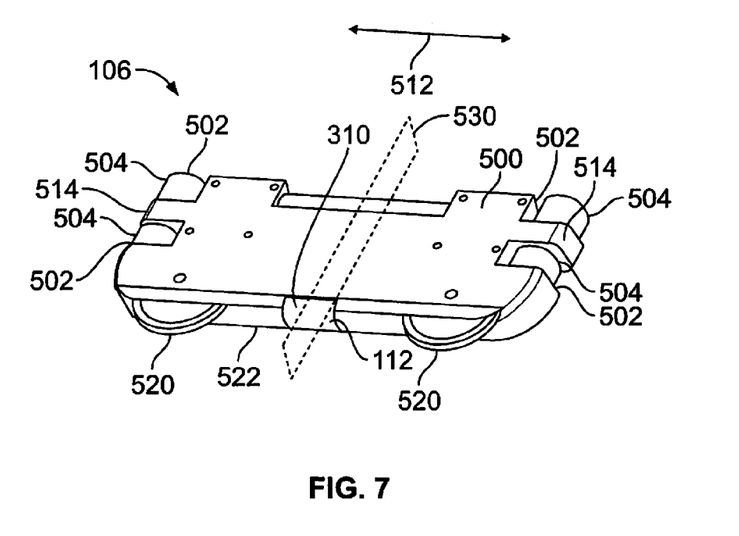
FIG. 7 illustrates a perspective top view of an inner ultrasound probe, according to an embodiment of the present disclosure.

FIG. 7 illustrates a perspective top view of the inner ultrasound probe 106, according to an embodiment of the present disclosure. As an example, the inner ultrasound probe 106 may be a 2.25 MHz ultrasound receiver. Alternatively, the inner ultrasound probe 106 may be various other types. The inner ultrasound probe 106 may include a main housing 500, such as a planar sheet or beam. The main housing 500 may include one or more roller chambers 502, each of which rotatably retains a wheel 504. The wheels 504 are configured to allow the inner ultrasound probe 106 to easily and smoothly slide over inner surfaces of a structure in the directions of arrows 512, such as in response to movement of the outer ultrasound probe 104 (shown in FIG. 6, for example). As shown, the wheels 504 are positioned at lateral edges 514 of the main housing 500. Alternatively, the wheels 504 may be positioned at various other positions. Also, more or less wheels 504 may be used. In at least one embodiment, the main housing 500 may not include any wheels.

Wheels 520 may also extend from front edge 522 of the main housing 500. The wheels 520 may be configured to abut into an interior surface of the curved leading edge of a structure (such as a winglet), to ensure smooth and easy movement of the inner ultrasound probe 106 therein. Alternatively, the inner ultrasound probe 106 may include more or less wheels than shown.

The single element transducer 112 may extend from the front edge 522. As shown, the single element transducer 112 may be aligned with a central lateral plane 530 that divides the inner ultrasound probe 106 into two equal halves. A central plane of the single element transducer 112 may be coplanar with the central lateral plane 530. Alternatively, the single element transducer 112 may be located at various other areas of the main housing 500.

As noted above, the main housing 500 may include one or more attractive elements, such as a metal, additional magnets, or the like, contained therein or positioned thereon. As an example, an attractive metal may be embedded within the main housing 500. The attractive metal is configured to be attracted to the magnets of the outer ultrasound probe 104 (shown in FIG. 6).

Figure 8:
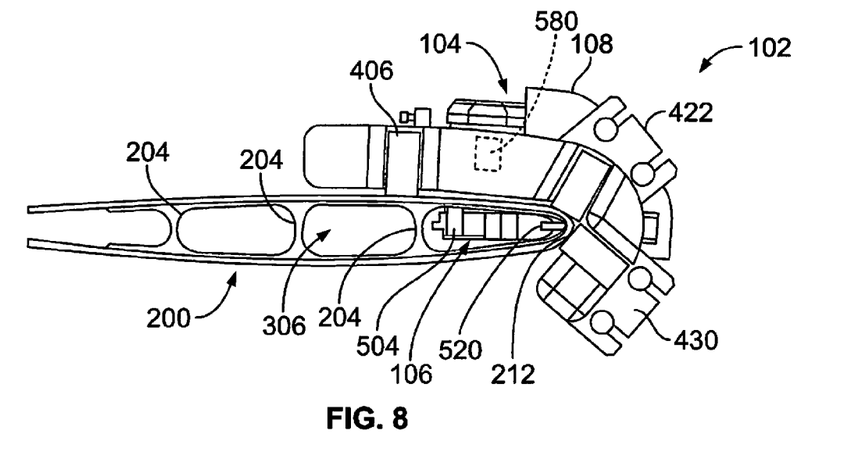
FIG. 8 illustrates an end view of an ultrasound scanning assembly being used to inspect an upper winglet, according to an embodiment of the present disclosure.

FIG. 8 illustrates an end view of the ultrasound scanning assembly 102 being used to inspect the upper winglet 200, according to an embodiment of the present disclosure. One or more magnets 580 within the outer ultrasound probe 104 magnetically couple the outer ultrasound probe 104 to the inner ultrasound probe 106. The inner ultrasound probe 106 is positioned within the internal cavity of the upper winglet 200, while the outer ultrasound probe 104 is positioned outside of the upper winglet 200, on an outer surface thereof. The phased array transducer 108 transmits ultrasound signals that are received by the single element transducer 112 (shown in FIGS. 1, 5, and 7, for example) of the inner ultrasound probe 106, as described above.

During a first pass over a length of the curved leading edge 212 of the upper winglet 200, the phased array transducer 108 may be secured to the upper securing brackets 422. During a second pass over a length of the curved leading edge 212, the phased array transducer 108 may be secured to the lower securing brackets 430.

Figure 9:
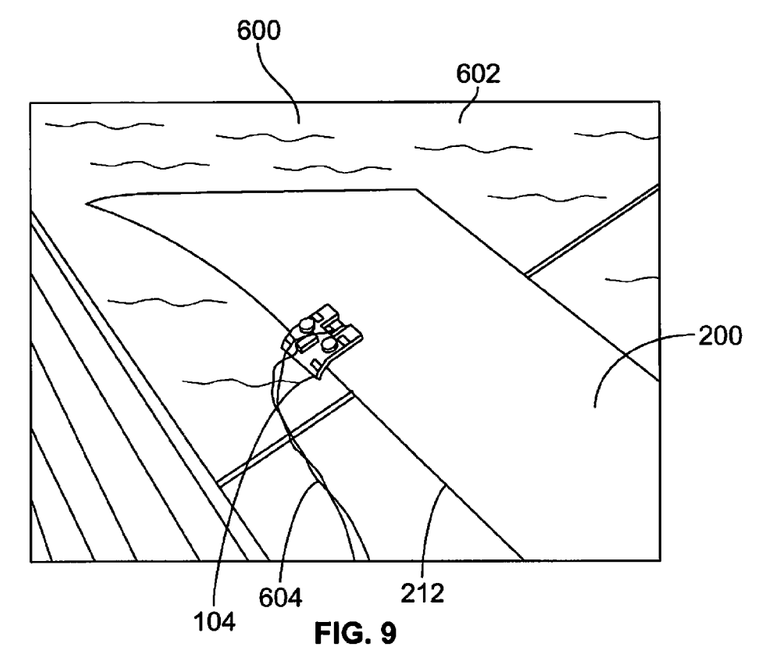
FIG. 9 illustrates a perspective top view of an outer ultrasound probe positioned on a curved leading edge of an upper winglet within a pool of water, according to an embodiment of the present disclosure.

FIG. 9 illustrates a perspective top view of the outer ultrasound probe 104 positioned on the curved leading edge 212 of the upper winglet 200 within a pool 600 of water 602, according to an embodiment of the present disclosure. The outer ultrasound probe 104 is magnetically coupled to the inner ultrasound probe 106, which is hidden from view in FIG. 9, as it is within the upper winglet 200. The upper winglet 200 may be submerged in the water 602, which may provide a medium that provides increased signal strength and transmission therethrough (as compared to air). The outer ultrasound probe 104 and/or the inner ultrasound probe 106 may connect to the control unit 103 (shown in FIG. 1), through one or more cables 604, for example.

Figure 10:
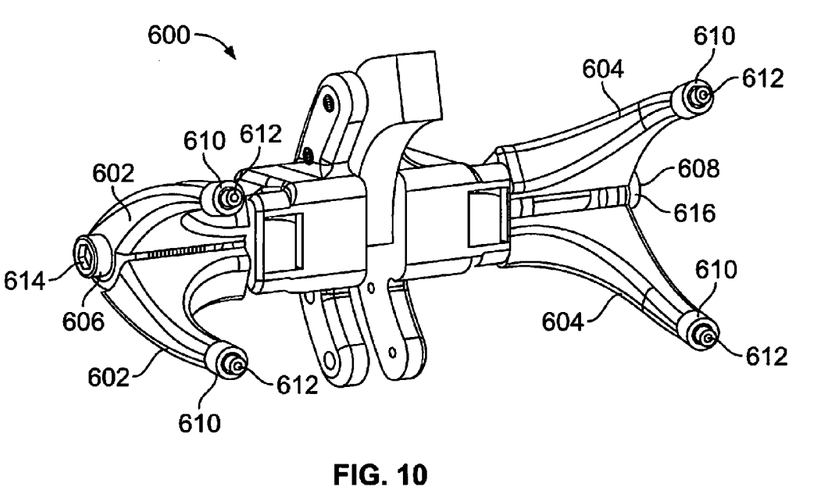
FIG. 10 illustrates a perspective view of an outer ultrasound probe, according to an embodiment of the present disclosure.

FIG. 10 illustrates a perspective view of an outer ultrasound probe 600, according to an embodiment of the present disclosure. The outer ultrasound probe 600 is similar to the outer ultrasound probe 104 described above. The outer ultrasound probe 600 may include two sets of opposed pivot arms 602 and 604 at opposite ends 606 and 608, respectively. Each pivot arm 602 and 604 includes a rotatable wheel 610 at a distal, free end 612. The pivot arms 602 pivotally connect at a pivot axis 614, while the pivot arms 604 pivotally connect a pivot axis 616. As such, the pivot arms 602 and 604 are configured to flex toward and away from another about the respective pivot axes 614 and 616. The pivot arms 602 and 604 may be spring biased toward another. That is, the pivot arms 602 and 604 may be inwardly-biased to conform to an outer surface of a structure. The biasing ensures that the pivot arms 602 and 604 securely clamp to portions of a structure, such as a winglet. As the outer ultrasound probe 600 translates over a surface of a structure, the pivot arms 602 and 604 may expand and contract to conform to the surface of the structure. The pivot arms 602 and 604 shown and described with respect to FIG. 10 may be used with respect to any of the outer ultrasound probes described in the present application.

Figure 11:
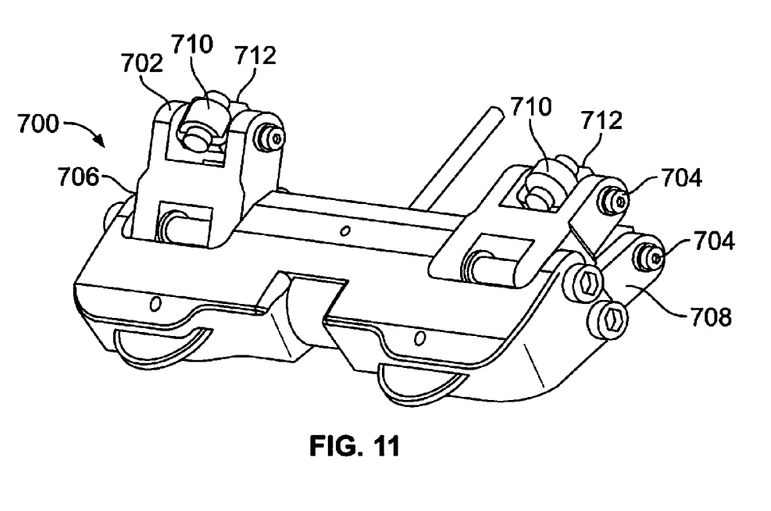
FIG. 11 illustrates a perspective view of an inner ultrasound probe, according to an embodiment of the present disclosure.

FIG. 11 illustrates a perspective view of an inner ultrasound probe 700, according to an embodiment of the present disclosure. The inner ultrasound probe 700 is similar to the inner ultrasound probe 106 described above. The inner ultrasound probe 700 may include two sets of opposed pivot arms 702 and 704 at opposite ends 706 and 708, respectively. Each pivot arm 702 and 704 includes a rotatable wheel 710 at a distal, free end 712. The pivot arms 702 pivotally connect at a pivot axis, while the pivot arms 704 pivotally connect at a pivot axis. As such, the pivot arms 702 and 704 are configured to flex away from and toward another about the respective pivot axes. The pivot arms 702 and 704 may be spring biased away from one another. That is, the pivot arms 702 and 704 may be outwardly-biased to conform to an inner surface of a structure. The biasing ensures that the pivot arms 702 and 704 securely abut into internal surfaces of a structure, such as a winglet. As the inner ultrasound probe 700 translates through a structure, the pivot arms 702 and 704 may expand and contract to conform to the surface of the structure. The pivot arms 702 and 704 shown and described with respect to FIG. 11 may be used with respect to any of the inner ultrasound probes described in the present application.

Figure 12:
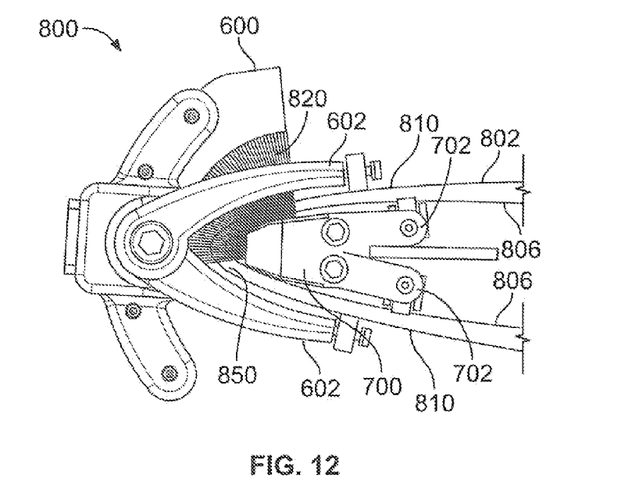
FIG. 12 illustrates an end view of an ultrasound scanning assembly being used to inspect a winglet, according to an embodiment of the present disclosure.

FIG. 12 illustrates an end view of an ultrasound scanning assembly 800 being used to inspect a winglet 802, according to an embodiment of the present disclosure. The ultrasound scanning assembly 800 includes the outer ultrasound probe 600 and the inner ultrasound probe 700, as described above. The inner ultrasound probe 700 is disposed within the winglet 802, such that the pivot arms 702 (and 704) are biased into inner surfaces 806 of the winglet 802. The pivot arms 602 (and 604) of the outer ultrasound probe 600 clamp to outer surfaces 810 of the winglet 802.

A phased array transducer within the outer ultrasound probe 600 transmits ultrasound signals 820 through a curved leading edge 850 of the winglet. The transmitted ultrasound signals 820 are received by a single element transducer within the inner ultrasound probe 700, as described above.

The outer and inner ultrasound probes 600 and 700, respectively, adjust to the contours of the curved leading edge 850, such as through the pivot arms 602, 604, 702, and 704. Magnets in one or both of the outer and inner ultrasound probes 600 and 700 magnetically couple the outer and inner ultrasound probes 600 and 700 together, as described above. After a first pass over a length of the curved leading edge 850, the outer ultrasound probe 600 may be turned upside down and re-positioned on the curved leading edge 850 to transmit the ultrasound signals 820 through a lower half of the curved leading edge 850.

Figure 13:
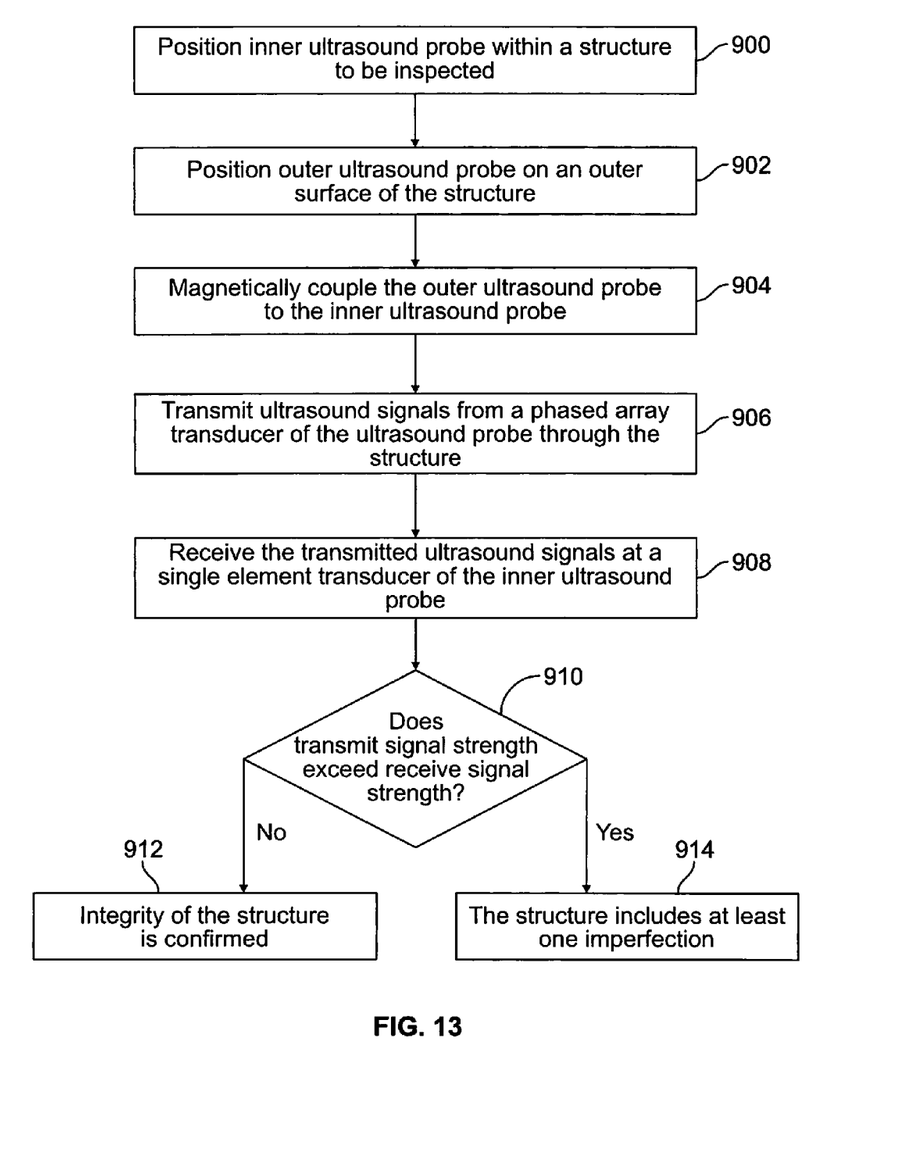
FIG. 13 illustrates a flow chart of a method of inspecting a structure, according to an embodiment of the present disclosure.

FIG. 13 illustrates a flow chart of a method of inspecting a structure, according to an embodiment of the present disclosure. At 900, an inner ultrasound probe is positioned within a structure to be inspected. At 902, an outer ultrasound probe is positioned on an outer surface of the structure. At 904, the outer ultrasound probe is magnetically coupled to the inner ultrasound probe.

At 906, ultrasound signals are transmitted from a phased array transducer of the outer ultrasound probe through the structure. At 908, the transmitted ultrasound signals are received by a single element transducer of the inner ultrasound probe. During the signal transmission and reception, the outer ultrasound probe may be moved over the structure. Because the outer ultrasound probe is magnetically coupled to the inner ultrasound probe, the inner ultrasound probe moves in response to movement of the outer ultrasound probe.

At 910, a signal strength of the transmitted signals is compared to a signal strength of the received signals. If the transmit signal strength does not exceed the receive signal strength (or does not exceed an expected difference), then the integrity of the structure is confirmed at 912. If, however, the transmit signal strength does exceed the receive signal strength (that is, the receive signal strength is less than the transmit signal strength), then it is determined at 914 that the structure includes at least one imperfection.

In at least one embodiment, the ultrasound scanning assembly may be configured to generate an image of the structure, including any imperfections, such as on a display screen that is operatively coupled to the control unit. As such, the ultrasound scanning assembly may be configured to identify and indicate on an image (displayed on a monitor, screen, or other such display) detected imperfections within a structure. An individual may review the image displayed and determine if the imperfection may be readily repaired or not.

Figure 14:
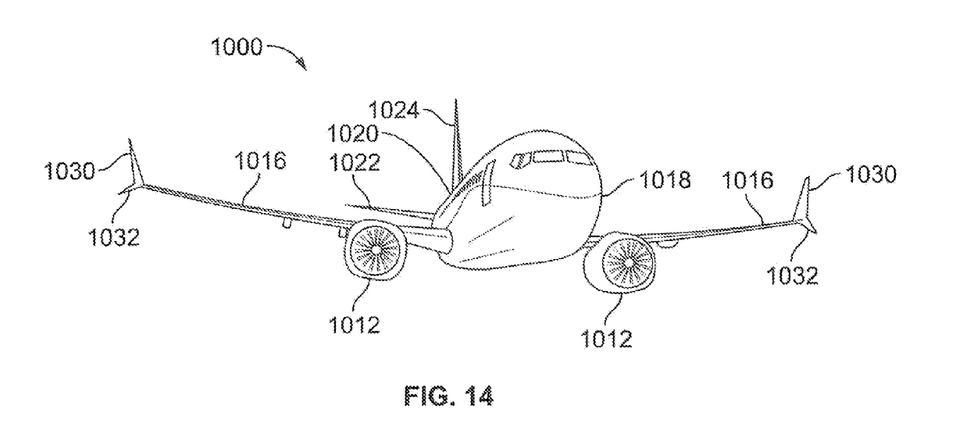
FIG. 14 illustrates a perspective front view of an aircraft, according to an embodiment of the present disclosure.

FIG. 14 illustrates a perspective front view of an aircraft 1000, according to an embodiment of the present disclosure. The aircraft 1000 may include a propulsion system that may include two turbofan engines 1012, for example. Optionally, the propulsion system may include more engines 1012 than shown. The engines 1012 are carried by wings 1016 of the aircraft 1000. In other embodiments, the engines 1012 may be carried by a fuselage 1018 and/or an empennage 1020. The empennage 1020 may also support horizontal stabilizers 1022 and a vertical stabilizer 1024.

An upper winglet 1030 and a lower winglet 1032 may be secured to a distal end of each wing 1016. The winglets 1030 and 1032 are examples of structures that may be inspected during a manufacturing process through the systems and methods described in the present application.

Referring to FIGS. 1-14, embodiments of the present disclosure provide systems and methods for efficiently inspecting structures, such an irregularly-shaped composite structures. Embodiments of the present disclosure provide systems and methods for efficiently inspecting winglets of an aircraft.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An ultrasound scanning assembly configured to inspect a composite winglet, the ultrasound scanning assembly comprising:
an outer ultrasound probe configured to be positioned on an outer surface of the composite winglet, wherein the outer ultrasound probe comprises: (a) a phased array transducer having a plurality of transducer elements, and (b) at least one inwardly-biased pivot arm that is configured to conform to the outer surface of the composite winglet; and
an inner ultrasound probe configured to be positioned within the composite winglet opposite from the outer surface, wherein the inner ultrasound probe comprises: (a) a single element transducer configured to receive ultrasound signals transmitted by the phased array transducer, and (b) at least one outwardly-biased pivot arm that is configured to conform to an inner surface of the composite winglet.

2. The ultrasound scanning assembly of claim 1, wherein one or both of the outer and inner ultrasound probes comprises at least one magnet that magnetically couples the outer and inner ultrasound probes together.

3. The ultrasound scanning assembly of claim 1, wherein the phased array transducer comprises a radially curved transmission surface.

4. The ultrasound scanning assembly of claim 1, wherein the single element transducer comprises a convex lens.

5. The ultrasound scanning assembly of claim 1, wherein the outer ultrasound probe comprises:

a main housing that retains the phased array transducer;
one or more wheels rotatably secured to the main housing, wherein the one or more wheels are configured to directly contact the outer surface of the composite winglet; and
one or more magnets coupled to the main housing, wherein the one or more magnets are configured to magnetically couple the outer ultrasound probe to the inner ultrasound probe.

6. The ultrasound scanning assembly of claim 5, wherein the phased array transducer is configured to be selectively secured at different positions of the main housing.

7. The ultrasound scanning assembly of claim 5, wherein the main housing comprises an inner curved surface that is configured to conform to the outer surface of the composite winglet.

8. The ultrasound scanning assembly of claim 1, wherein the inner ultrasound probe comprises:
a main housing that retains the single transducer element; and
one or more wheels rotatably secured to the main housing, wherein the one or more wheels are configured to directly contact an inner surface of the structure.

9. An ultrasound scanning system configured to inspect a composite winglet, the ultrasound scanning system comprising:
an ultrasound scanning assembly including:
an outer ultrasound probe configured to be positioned on an outer surface of the composite winglet, wherein the outer ultrasound probe comprises a phased array transducer having a plurality of transducer elements; and
an inner ultrasound probe magnetically coupled to the outer ultrasound probe, wherein the inner ultrasound probe is configured to be positioned within an internal cavity of the composite winglet and abut into an inner surface of the composite winglet that is opposite from the outer surface, wherein the inner ultrasound probe comprises a single element transducer configured to receive ultrasound signals transmitted by the phased array transducer; and
a control unit in communication with the ultrasound scanning assembly, wherein the control unit is configured to compare a transmit signal strength of ultrasound signals transmitted from the outer ultrasound probe with a receive signal strength of the ultrasound signals received by the single element transducer, wherein the control unit is configured to determine an existence of one or more imperfections within the composite winglet by comparing the transmit signal strength with the receive signal strength.

10. The ultrasound scanning system of claim 9, wherein the phased array transducer comprises a radially curved transmission surface, and wherein the single element transducer comprises a convex lens.

11. The ultrasound scanning system of claim 9, wherein the outer ultrasound probe comprises:
a main housing that retains the phased array transducer;
one or more wheels rotatably secured to the main housing, wherein the one or more wheels are configured to directly contact the outer surface of the winglet; and
one or more magnets coupled to the main housing, wherein the one or more magnets are configured to magnetically couple the outer ultrasound probe to the inner ultrasound probe.

12. The ultrasound scanning system of claim 11, wherein the phased array transducer is configured to be selectively secured at different positions of the main housing.

13. The ultrasound scanning system of claim 11, wherein the main housing comprises an inner curved surface that is configured to conform to the outer surface of a curved leading edge of the composite winglet.

14. The ultrasound scanning system of claim 9, wherein the inner ultrasound probe comprises:
a main housing that retains the single transducer element; and
one or more wheels rotatably secured to the main housing, wherein the one or more wheels are configured to directly contact the inner surface of the composite winglet.

15. The ultrasound scanning system of claim 9, wherein the outer ultrasound probe comprises at least one inwardly-biased pivot arm that is configured to conform to the outer surface of a curved leading edge of the composite winglet.

16. The ultrasound scanning system of claim 9, wherein the inner ultrasound probe comprises at least one outwardly-biased pivot arm that is configured to conform to the inner surface of the composite winglet.

17. A method for inspecting a composite winglet, the method comprising:
positioning an outer ultrasound probe on an outer surface of the composite winglet;
positioning an inner ultrasound probe within the composite winglet;
magnetically coupling the outer ultrasound probe to the inner ultrasound probe;
transmitting ultrasound signals from a radially-curved transmission surface of a phased array transducer of the outer ultrasound probe through the composite winglet toward a single element transducer of the inner ultrasound probe;
comparing a transmit signal strength of the ultrasound signals transmitted from the phased array transducer to a receive signal strength of the ultrasound signals received by the single element transducer;
confirming a structural integrity of the composite winglet in response to the receive signal strength agreeing with the transmit signal strength; and
indicating a presence of an imperfection within the composite winglet in response to the receive signal strength differing from the transmit signal strength.

18. The method of claim 17, further comprising:
moving the outer ultrasound probe over the outer surface of the composite winglet; and
moving the inner ultrasound probe through the interior of the composite winglet in response to the outer ultrasound probe moving over the outer surface of the composite winglet.

19. A method for inspecting a composite winglet, the method comprising:
positioning an outer ultrasound probe on an outer surface of the composite winglet, wherein the outer ultrasound probe comprises at least one inwardly-biased pivot arm that is configured to conform to the other surface of the composite winglet;
positioning an inner ultrasound probe within the composite winglet, wherein the inner ultrasound probe comprises at least one outwardly-biased pivot arm that is configured to conform to an inner surface of the composite winglet;

transmitting ultrasound signals from a phased array transducer of the outer ultrasound probe through the composite winglet toward a single element transducer of the inner ultrasound probe;

comparing a transmit signal strength of the ultrasound signals transmitted from the phased array transducer to a receive signal strength of the ultrasound signals received by the single element transducer;

confirming a structural integrity of the composite winglet in response to the receive signal strength agreeing with the transmit signal strength; and indicating a presence of an imperfection within the composite winglet in response to the receive signal strength differing from the transmit signal strength.

20. The method of claim 19, further comprising:

moving the outer ultrasound probe over the outer surface of the composite winglet; and moving the inner ultrasound probe through the interior of the composite winglet in response to the outer ultrasound probe moving over the outer surface of the composite winglet.

\* \* \* \* \*